US00PP27116P2

(12) United States Plant Patent
Beekenkamp

(10) Patent No.: US PP27,116 P2
(45) Date of Patent: Aug. 30, 2016

(54) ***BEGONIA* PLANT NAMED 'BKPBEEEP'**

(50) Latin Name: *Begonia hiemalis*
Varietal Denomination: BKPBEEEP

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 95 days.

(21) Appl. No.: 14/121,888

(22) Filed: Oct. 31, 2014

(51) Int. Cl.
*A01H 5/02* (2006.01)

(52) U.S. Cl.
USPC ..... Plt./343

(58) Field of Classification Search
USPC ..... Plt./343
See application file for complete search history.

*Primary Examiner* — Susan McCormick Ewoldt
(74) *Attorney, Agent, or Firm* — C. A. Whealy

(57) ABSTRACT

A new and distinct cultivar of *Begonia* plant named 'BKPBEEEP', characterized by its upright, somewhat outwardly spreading and mounded plant habit; freely basal branching habit; dark green-colored leaves; uniform and freely flowering habit; and double flowers that are dark pink in color.

2 Drawing Sheets

Botanical designation: *Begonia hiemalis.*
Cultivar denomination: 'BKPBEEEP'.

BACKGROUND OF THE INVENTION

The present invention relates to a new and distinct cultivar of *Begonia* plant, botanically known as *Begonia hiemalis*, commercially referred to as Elatior *Begonia* and hereinafter referred to by the name 'BKPBEEEP'.

The new *Begonia* plant is a product of a planned breeding program conducted by the Inventor in Maasdijk, The Netherlands. The objective of the breeding program was to develop new freely branching and freely flowering *Begonia* plants with large attractive flowers.

The new *Begonia* plant originated from a cross-pollination made by the Inventor in April, 2010 of a proprietary selection of *Begonia hiemalis* identified as code number 6501087, not patented, as the female, or seed, parent with a proprietary selection of *Begonia hiemalis* identified as code number 6500604, not patented, as the male, or pollen, parent. The new *Begonia* plant was discovered and selected by the Inventor as a single flowering plant from within the progeny of the stated cross-pollination in a controlled greenhouse environment in Maasdijk, The Netherlands in December, 2010.

Asexual reproduction of the new *Begonia* plant by tip cuttings in a controlled greenhouse environment in Maasdijk, The Netherlands since March, 2011 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBEEEP'. These characteristics in combination distinguish 'BKPBEEEP' as a new and distinct *Begonia* plant:

1. Upright, somewhat outwardly spreading and mounded plant habit.
2. Freely basal branching habit.
3. Dark green-colored leaves.
4. Uniform and freely flowering habit.
5. Double flowers that are dark pink in color.

Plants of the new *Begonia* can be compared to plants of the female parent selection. Plants of the new *Begonia* differ primarily from plants of the female parent selection in the following characteristics:

1. Plants of the new *Begonia* have sparsely pubescent stems whereas plants of the female parent selection have moderately pubescent stems.
2. Plants of the new *Begonia* have slightly lighter green-colored leaves than plants of the female parent selection.
3. Plants of the new *Begonia* have smaller flowers than plants of the female parent selection.

Plants of the new *Begonia* can be compared to plants of the male parent selection. Plants of the new *Begonia* differ primarily from plants of the male parent selection in the following characteristics:

1. Plants of the new *Begonia* have darker green-colored leaves than plants of the male parent selection.
2. Plants of the new *Begonia* have larger flowers than plants of the male parent selection.
3. Flower tepals of plants of the new *Begonia* are dark pink in color whereas flower tepals of plants of the male parent selection are pale pink in color.

Plants of the new *Begonia* can be compared to plants of the *Begonia hiemalis* 'BBDRA', disclosed in U.S. Plant Pat. No. 19,700. In side-by-side comparisons conducted in Maasdijk, The Netherlands, plants of the new *Begonia* differed from plants of 'BBDRA' in the following characteristics:

1. Plants of the new *Begonia* had fewer tepals per flower than plants of 'BBDRA'.

2. Plants of the new *Begonia* and 'BBDRA' differed slightly in flower color.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'BKPBEEEP' grown in a container.

The photograph on the second sheet are close-up views of upper and lower surfaces of typical flowers and leaves of 'BKPBEEEP'.

DETAILED BOTANICAL DESCRIPTION

Plants used for the aforementioned photographs and following observations and measurements were grown in 13-cm containers during the summer in a glass-covered greenhouse in Maasdijk, The Netherlands. During the production of the plants, day temperatures ranged from 20° to 21° C. and night temperatures ranged from 19° to 20° C. Plants were ten weeks old when the photographs and the description were taken. In the following description, color references are made to The Royal Horticultural Society Colour Chart, 2007 Edition, except where general terms of ordinary dictionary significance are used.

Botanical classification: *Begonia hiemalis* 'BKPBEEEP'.

Parentage:

*Female, or seed, parent*.—Proprietary selection of *Begonia hiemalis* identified as code number 6501087, not patented.

*Male, or pollen, parent*.—Proprietary selection of *Begonia hiemalis* identified as code number 6500604, not patented.

Propagation:

*Type*.—By tip cuttings.

*Time to initiate roots*.—About 20 days at temperatures about 25° C.

*Time to produce a rooted young plant*.—About 35 to 36 days at temperatures about 21° C. to 23° C.

*Root description*.—Fine, fibrous; light brown in color; plants of the new *Begonia* have not been observed to form tubers.

*Rooting habit*.—Moderate freely branching; medium density.

Plant description:

*Plant and growth habit*.—Upright, somewhat outwardly spreading and mounded plant habit; plant shape roughly broadly ovate to globular; freely basal branching with about five basal branches developing per plant; moderately vigorous growth habit.

*Plant height*.—About 27.5 cm.

*Plant width*.—About 30.7 cm.

*Lateral branch description*.—Length: About 14.2 cm. Diameter: About 1.2 cm. Internode length: About 3.5 cm. Texture: Sparsely pubescent. Aspect: Upright to about 50° from the vertical. Color, developing and fully developed: Close to between 152A and 199A.

*Leaf description*.—Arrangement: Alternate, simple. Length: About 15.4 cm. Width: About 11.7 cm. Shape: Ovate to broadly ovate. Apex: Acute. Base: Oblique. Margin: Serrulate, undulate. Texture, upper surface: Smooth, glabrous; velvety. Texture, lower surface: Sparsely pubescent along veins. Venation pattern: Palmate. Color: Developing leaves, upper surface: Close to between 143A and 146A. Developing leaves, lower surface: Close to 147C. Fully expanded leaves, upper surface: Darker than between 139A and N189A; venation, close to 143A. Fully expanded leaves, lower surface: Close to 178A to 178B; venation, close to 148A. Petioles: Length: About 6.5 cm. Diameter: About 8 mm. Texture, upper and lower surfaces: Sparsely pubescent. Color, upper surface: Close to 152A tinged with close to 176B; distally, close to 178C. Color, lower surface: Close to 152A slightly tinged with close to 176B.

Flower description:

*Flowering habit*.—Double rotate flowers arranged in axillary compound cymes; flowers sterile; freely flowering habit with about 8 to 14 flowers per cyme and about 200 flowers developing per plant; flowers face upright to outwardly.

*Fragrance*.—None detected.

*Natural flowering season*.—Plants begin flowering about 54 days after planting; long flowering period, plants flower freely and continuously from spring into the autumn in The Netherlands.

*Flower longevity*.—Individual flowers last about ten days on the plant; flowers not persistent.

*Inflorescence height*.—About 18 cm.

*Inflorescence diameter*.—About 8.4 cm.

*Flower diameter*.—About 5.5 cm.

*Flower height*.—About 2 cm.

*Flower buds*.—Length: About 1.8 cm. Diameter: About 7 mm to 26 mm. Shape: Reniform to orbicular, flattened. Color: Close to 53C to 53D.

*Tepals*.—Quantity per flower and arrangement: Two, opposite. Length: About 3.1 cm. Width: About 4.3 cm. Shape: Reniform. Apex: Rounded. Margin: Entire. Texture, upper surface: Smooth, glabrous; velvety. Texture, lower surface: Smooth, glabrous; slightly velvety. Color: When opening, upper surface: Close to 54A to 54B. When opening, lower surface: Close to 48B; towards the margins, close to 52B. Fully opened, upper surface: Close to 58C; towards the margins, close to 58B; color does not fade with development. Fully opened, lower surface: Close to 52C; towards the margins, close to 52B; color does not fade with development.

*Tepaloids*.—Quantity per flower and arrangement: About 30 in multiple whorls. Length: About 1.7 cm. Width: About 1.5 cm. Shape: Obovate to orbicular. Apex: Rounded. Margin: Entire. Texture, upper surface: Smooth, glabrous; velvety. Texture, lower surface: Smooth, glabrous; slightly velvety. Color: When opening, upper surface: Close to 58B; inner tepaloids, towards the base, close to 12A. When opening, lower surface: Close to 58C; inner tepaloids, towards the base, close to 12A. Fully opened, upper surface: Close to 58B and 58C; inner tepaloids, towards the base, close to 12A; color does not fade with development. Fully opened, lower surface: Close to 58C and 58D; inner tepaloids, towards the base, close to 12A; color does not fade with development.

*Peduncles*.—Length: About 11.6 cm. Diameter: About 5 mm. Angle: About 30° from branch axis. Strength: Flexible, bending with the weight of the flowers. Texture: Smooth, glabrous. Color: Close to 152A.

*Pedicels*.—Length: About 1.9 cm. Diameter: About 2 mm. Angle: About 30° from the peduncle axis. Strength: Flexible, bending with the weight of the flowers. Texture: Smooth, glabrous. Color: Close to 176C.

*Reproductive organs*.—Androecium: Not observed on plants of the new *Begonia*. Gynoecium: Not observed on plants of the new *Begonia*.

Disease & pest resistance: Resistance to pathogens and pests common to *Begonia* plants has not been observed on plants of the new *Begonia*.

Temperature tolerance: Plants of the new *Begonia* have been observed to tolerate high temperatures of about 35° C. and to be hardy to USDA Hardiness Zone 10.

It is claimed:

1. A new and distinct *Begonia* plant named 'BKPBEEEP' as illustrated and described.

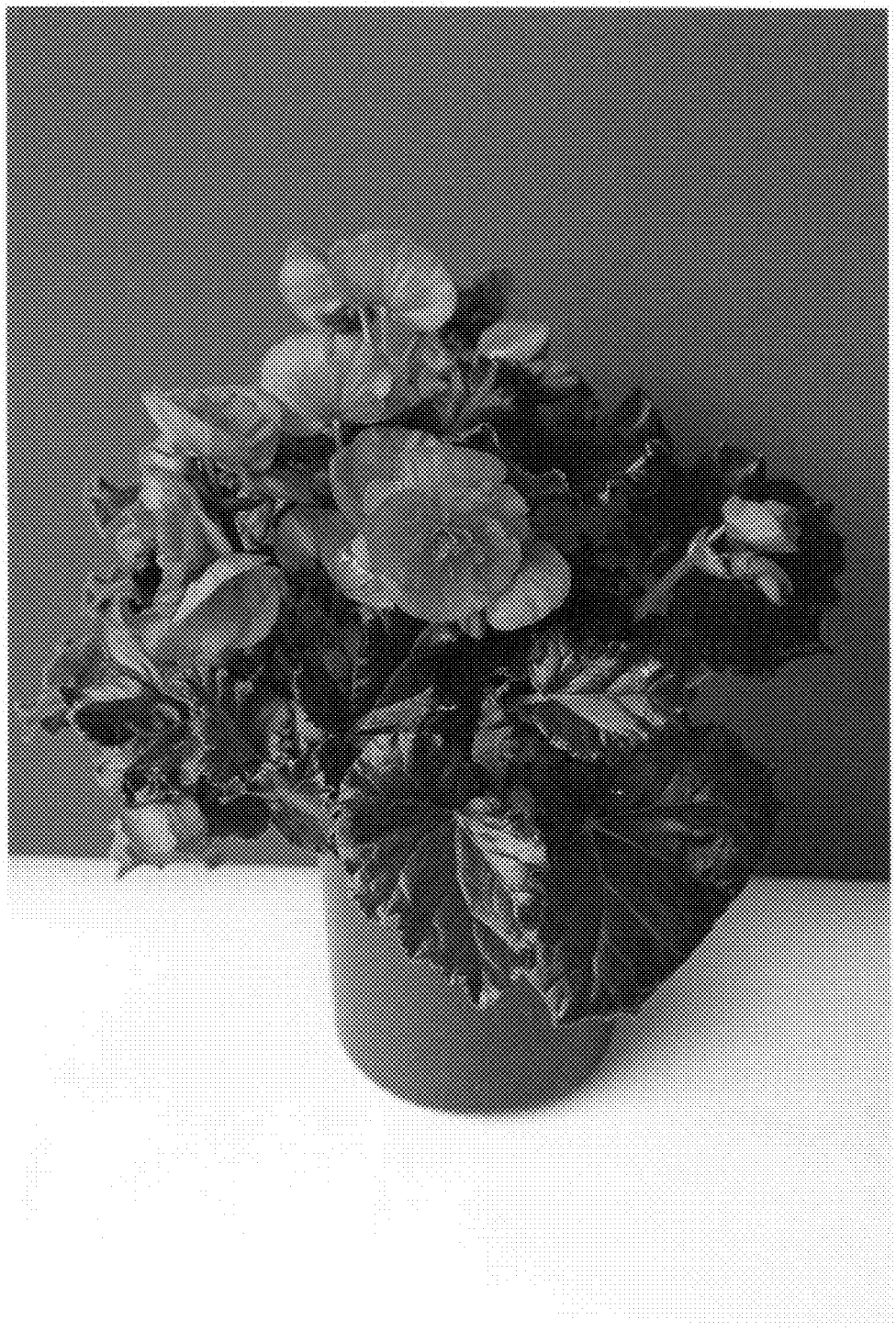

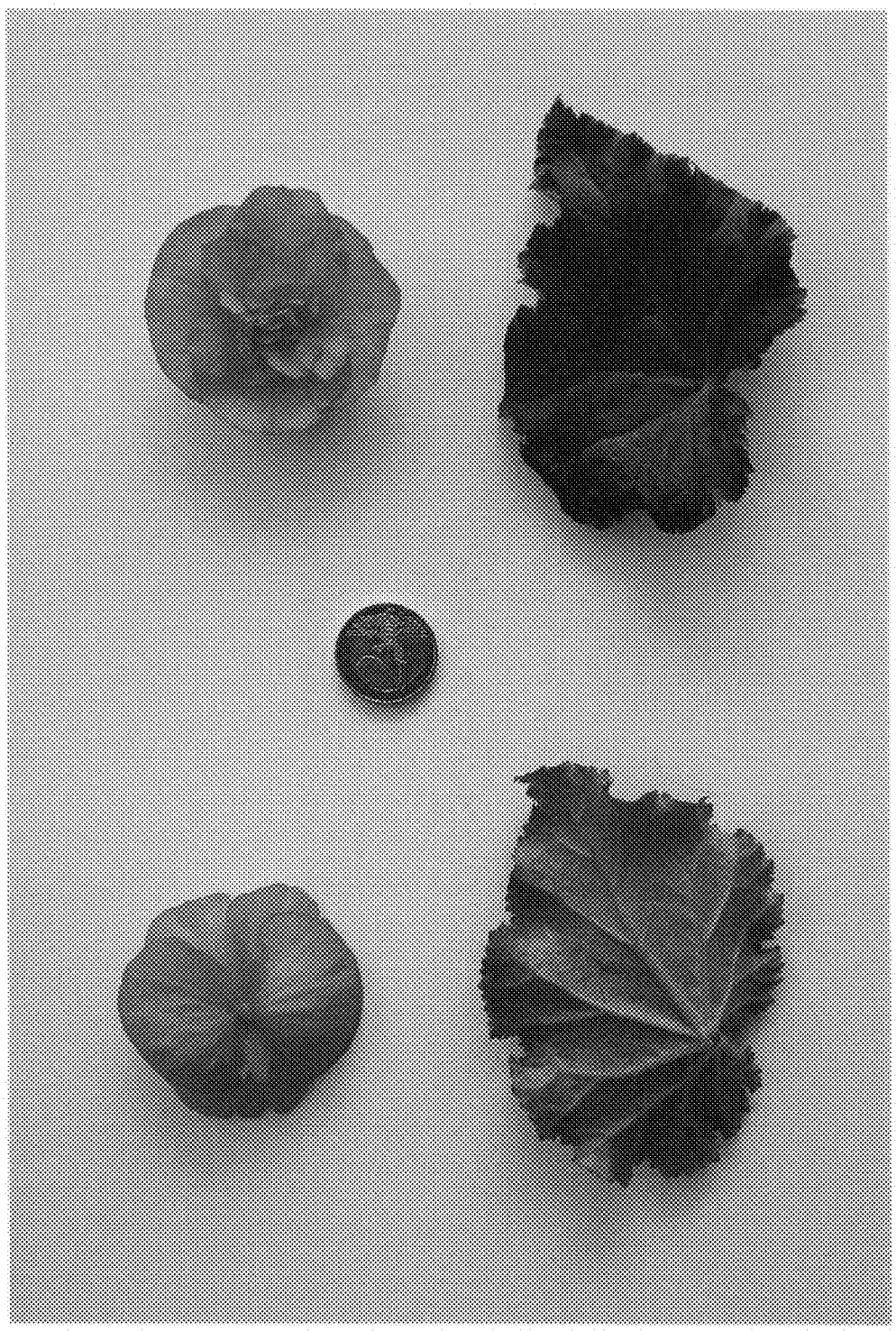

* * * * *